United States Patent
De Bruijn et al.

(10) Patent No.: US 9,237,844 B2
(45) Date of Patent: Jan. 19, 2016

(54) SYSTEM AND METHOD FOR TRACKING THE POINT OF GAZE OF AN OBSERVER

(75) Inventors: Frederik Jan De Bruijn, Eindhoven (NL); Karl Catharina Van Bree, Eindhoven (NL); Tommaso Gritti, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 341 days.

(21) Appl. No.: 13/582,582

(22) PCT Filed: Mar. 15, 2011

(86) PCT No.: PCT/IB2011/051076
§ 371 (c)(1),
(2), (4) Date: Sep. 4, 2012

(87) PCT Pub. No.: WO2011/117776
PCT Pub. Date: Sep. 29, 2011

(65) Prior Publication Data
US 2013/0002846 A1    Jan. 3, 2013

(30) Foreign Application Priority Data
Mar. 22, 2010 (EP) .................................. 10157169

(51) Int. Cl.
*A61B 3/113* (2006.01)
*G06F 3/01* (2006.01)
(Continued)

(52) U.S. Cl.
CPC ................ *A61B 3/113* (2013.01); *G06F 3/013* (2013.01); *G06F 3/147* (2013.01); *G06K 9/0061* (2013.01); *G09G 2380/12* (2013.01)

(58) Field of Classification Search
CPC ... G06F 3/013; G06F 3/0425; G06K 9/00597; H04N 5/23219; H04N 13/0014; H04N 13/0468; H04N 19/00248
USPC ............................. 348/78, 159; 351/209, 210
See application file for complete search history.

(56) References Cited

U.S. PATENT DOCUMENTS

| 4,973,149 | A |   | 11/1990 | Hutchinson |
|-----------|---|---|---------|------------|
| 5,204,703 | A | * | 4/1993  | Hutchinson et al. .......... 351/210 |
| 6,659,611 | B2 | * | 12/2003 | Amir et al. .................... 351/210 |

(Continued)

FOREIGN PATENT DOCUMENTS

| CN | 101172034 A | 5/2008 |
|----|-------------|--------|
| WO | 2005046465 A1 | 5/2005 |
| WO | 2008085272 A1 | 7/2008 |

OTHER PUBLICATIONS

Travis et al: "Manufacturing Requirements for High Quality Flat Projection Displays"; IDMC 2005, pp. 229-232.
(Continued)

*Primary Examiner* — Brian Yenke

(57) ABSTRACT

A system for tracking the point of gaze of an observer observing an object comprises a camera for recording an image of an eye of the observer, comprises a means for providing a luminous marker, and means for analyzing the image of the eye to determine the reflection of the marker on the eye and the centre of the pupil. The relative positions of the corneal reflection of the marker and the pupil centre are measured. The marker is repositioned, in dependence on the determined relative positions, to improve correspondence between the corneal reflection of the marker and the pupil center.

18 Claims, 13 Drawing Sheets

(51) Int. Cl.
*G06F 3/147* (2006.01)
*G06K 9/00* (2006.01)

(56) References Cited

U.S. PATENT DOCUMENTS

| | | | | |
|---|---|---|---|---|
| 6,757,422 B1* | 6/2004 | Suzuki et al. | | 382/154 |
| 7,306,337 B2* | 12/2007 | Ji et al. | | 351/209 |
| 7,391,887 B2* | 6/2008 | Durnell | | 382/117 |
| 7,686,451 B2* | 3/2010 | Cleveland | | 351/210 |
| 7,809,160 B2* | 10/2010 | Vertegaal et al. | | 382/103 |
| 7,963,652 B2* | 6/2011 | Vertegaal et al. | | 351/205 |
| 7,986,816 B1* | 7/2011 | Hoanca et al. | | 382/115 |
| 8,032,842 B2* | 10/2011 | Kwon | G06K 9/00604 | |
| | | | | 351/209 |
| 8,077,914 B1* | 12/2011 | Kaplan | | 382/103 |
| 8,317,327 B2* | 11/2012 | Cleveland et al. | | 351/209 |
| 8,483,567 B2* | 7/2013 | Armentrout et al. | | 398/118 |
| 8,500,278 B2* | 8/2013 | Lo | A61B 3/024 | |
| | | | | 351/206 |
| 8,562,136 B2* | 10/2013 | Blixt et al. | | 351/210 |
| 8,632,182 B2* | 1/2014 | Chen et al. | | 351/219 |
| 8,749,396 B2* | 6/2014 | Maggiore | | 340/686.1 |
| 8,810,647 B2* | 8/2014 | Niclass et al. | | 348/135 |
| 8,814,691 B2* | 8/2014 | Haddick et al. | | 463/42 |
| 8,854,447 B2* | 10/2014 | Conness et al. | | 348/78 |
| 8,937,591 B2* | 1/2015 | Julian | | 345/157 |
| 2003/0098954 A1* | 5/2003 | Amir et al. | | 351/210 |
| 2003/0123027 A1 | 7/2003 | Amir et al. | | |
| 2004/0196433 A1* | 10/2004 | Durnell | | 351/209 |
| 2005/0175218 A1* | 8/2005 | Vertegaal et al. | | 382/103 |
| 2006/0082542 A1* | 4/2006 | Morita et al. | | 345/156 |
| 2006/0109238 A1* | 5/2006 | Lau et al. | | 345/156 |
| 2006/0110008 A1 | 5/2006 | Vertegaal et al. | | |
| 2006/0139319 A1* | 6/2006 | Kariathungal et al. | | 345/156 |
| 2007/0081090 A1* | 4/2007 | Singh | | 348/333.11 |
| 2007/0177103 A1* | 8/2007 | Migliaccio et al. | | 351/206 |
| 2008/0089090 A1* | 4/2008 | Bathiche et al. | | 362/600 |
| 2008/0120141 A1* | 5/2008 | Kariathungal et al. | | 705/3 |
| 2009/0180071 A1* | 7/2009 | Fateh | | 351/203 |
| 2009/0219484 A1* | 9/2009 | Ebisawa | | 351/210 |
| 2009/0245696 A1* | 10/2009 | Yuan et al. | | 382/312 |
| 2009/0315827 A1* | 12/2009 | Elvesjo et al. | | 345/157 |
| 2010/0066975 A1 | 3/2010 | Rehnstrom | | |
| 2010/0080447 A1* | 4/2010 | Kanazawa et al. | | 382/154 |
| 2010/0128118 A1* | 5/2010 | Swindells et al. | | 348/78 |
| 2010/0201621 A1* | 8/2010 | Niikawa | | 345/158 |
| 2010/0220288 A1* | 9/2010 | Cleveland | | 351/206 |
| 2010/0225617 A1* | 9/2010 | Yoshimoto et al. | | 345/175 |
| 2011/0037849 A1* | 2/2011 | Niclass et al. | | 348/135 |
| 2012/0127140 A1* | 5/2012 | Ryan | G09G 3/3648 | |
| | | | | 345/207 |
| 2013/0243258 A1* | 9/2013 | Hennessey et al. | | 382/103 |
| 2013/0265227 A1* | 10/2013 | Julian | | 345/157 |
| 2013/0328763 A1* | 12/2013 | Latta et al. | | 345/156 |
| 2014/0003738 A1* | 1/2014 | Williams et al. | | 382/282 |
| 2014/0253589 A1* | 9/2014 | Tout et al. | | 345/633 |

OTHER PUBLICATIONS

Mulligan: "Optical Eye Models for Gaze Tracking"; ETRA 2006, ISBN 1-59593-305-0/06/0003, p. 51.
Duchowski: "Eye Tracking Methodology: Theory and Practice"; Second Edition, Springer-Verlag Publishers, 2007.
Glenstrup et al: "Eye Controlled Media: Present and Future State"; Thesis. University of Copenhagen, Jun. 1995, 90 Page Document.
Ohno: "One-Point Calibration Gaze Tracking Method"; ACM, ETRA 2006, p. 34.
Vertegaal et al: "Look Who'S Talking: The Gaze Groupware System"; CHI'98. pp. 293-294.
Hennessey: "A Single Camera Eye-Gaze Tracking System With Free Head Motion"; ETRA 2006, ACM 1-59593-305-0/06/0003, pp. 87-94.
Sibert et al: "Evaluation of Eye Gaze Interaction"; CHI'00 Proceedings of the Sigchi Conference on Human Factors in Computing Systems, pp. 281-288.
Shell et al:"Eyepliances: Attention-Seeking Devices That Respond to Visual Attention"; CHI 2003, ACM 1-58113-630, 2 Page Document.
Ebisawa: "Improved Video-Based Eye-Gaze Detection Method"; IEEE Transactions on Instrumentation and Measurement, vol. 47, No. 4, Aug. 1998, pp. 948-955.
Hiley: "A Human Computer Interface Based on Real Time Eye Tracking"; Thesis, 2006 71 Page Document.
Guestrin et al: "General Theory of Remote Gaze Estimation Using the Pupil Center and Corneal Reflections"; IEEE Transactions on Biomedical Engineering, vol. 53, No. 6, Jun. 2006, pp. 1124-1133.
BASF The Chemical Company: "Laser Transmission Welding of Colored and Transparent Polymers"; Advertisement, 2009, 6 Pages.

* cited by examiner ations.

SYSTEM AND METHOD FOR TRACKING THE POINT OF GAZE OF AN OBSERVER

FIELD OF THE INVENTION

The invention relates to a system for tracking the point of gaze of an observer observing an object, wherein the system comprises a device for recording an image of an eye of the observer, comprises a means for providing a luminous marker on or associated with the observed object, and a means for determining from the image a corneal reflection of the marker and the centre of the pupil.

The invention further relates to a method for tracking the point of gaze of an observer observing an object, wherein the method comprises recording an image of an eye of the observer, providing a luminous marker on or associated with the observed object, and determining from the image a corneal reflection of the marker and the centre of the pupil.

BACKGROUND OF THE INVENTION

A system and method of the above type is known from US patent application US 2006/0110008.

In this document a number of markers are provided and at least one marker of which the corneal reflection is within a threshold distance of the pupil centre is identified or at least two markers having a corneal reflection close to the centre of the pupil. The identified marker or markers are indicative of the observer's point of gaze at the object.

Continuous measurement of the viewing direction or also called gaze is commonly referred to as 'gaze-tracking' (often the more ambiguous term 'eye-tracking' is used). There are various methods to perform gaze tracking Video capture has shown to be a viable option for remote and truly unobtrusive gaze tracking. However, virtually all gaze tracking systems require a user-specific calibration after which the user is allowed only little head movement. Consequently, these systems are confined to desktop usage and not suitable for consumer applications. In consumer applications, user-specific calibration is not a realistic option. Calibration-free gaze tracking is widely pursued by several research centres, often by extrapolating on the basis of existing concepts (more cameras, more processing). The observer can be a human, whether an adult or a child, but also an animal.

US 2006/0110008 attempts to remedy the problem and to provide a calibration-free system and method. In the situation that the eye is gazing at a light source, its reflection in the cornea appears to coincide with the pupil centre. The system and method of 2006/011008 provides a number of markers on the object. In the recorded image of eye the marker having a corneal reflection within a threshold distance of the pupil centre, or a number of markers having a corneal reflection close to the pupil centre are identified. These are used to estimate the direction of gaze.

However, the known system has a number of shortcomings:

each of the markers has to be labelled. This condition requires a number of video frames to be analysed before identification of a marker can be made. This introduces latency in the gaze tracking. Given the motility of the eye, temporal latency quickly gives rise to motion artefacts.

Where one marker is used, there is always an inaccuracy equivalent to the threshold distance in the accuracy of the established gaze direction.

Where more than one marker is used interpolation is required. This requires computation power and introduces inaccuracies.

SUMMARY OF THE INVENTION

It is an object of the invention to provide a system and method in which the speed of gaze tracking and/or accuracy is improved.

To that end, the system is a system comprising a means for determining relative positions of the corneal reflection of the marker and the pupil centre and a means for repositioning the marker dependent on the determined relative positions.

The method is a method wherein relative positions of the corneal reflection of the marker and the pupil centre are determined and the marker is repositioned dependent on the determined relative positions.

In the system and method of the invention temporal latency is reduced since the marker is not a static marker but is repositioned on the basis of feedback of measurements of the relative positions of the corneal reflection of the marker and the pupil centre. The marker is repositioned, i.e. the position of the marker on or associated with the observed object is changed, to improve the correspondence between the corneal reflection of the marker and the pupil centre, preferably to have the corneal reflection of the marker and the pupil centre coincide or almost coincide. When the corneal reflection and the pupil centre coincide, the direction of gaze can be accurately determined since the position of the marker on or associated with the observed object then indicates the direction of gaze to a high degree of accuracy.

The observer can be and in many circumstances will be a human, but within the method and system in accordance with the invention the observer can also be a non-human observer, for instance animals in animal studies so as for instance to study the gaze of such animals as dogs or primates.

The system and method provides, in respect of prior methods a number of advantages:

The system and method do not require user-dependent calibration, in contrast to many current solutions.

The system and method are based on an optical property of the eye that is largely independent of head position and orientation and virtually invariant among different individuals.

The system and method allow a freedom of head movement far beyond that of existing gaze tracking systems. This is an essential step in enabling the use of gaze tracking for consumer applications.

In respect to the system and method of US 2006/0110008 there is no need to label the separate markers or groups of markers with unique identifiers. The known system uses temporal light modulation to encode the different identifiers which introduces a temporal latency (expressed in number of frames) that is proportional to the code length. The system and method of the invention responds much faster, and the feedback system has shown to converge faster, often within a single frame delay. Compared to the system and method of US 2006/011008 the correspondence between corneal reflection of the marker and the pupil centre can be much improved, reducing inaccuracies. By having the reflection of the marker and the pupil centre coincide any inaccuracy due to the threshold value in US 2006/0110008 is reduced or minimized.

The system and method in accordance with the invention use a means for repositioning the marker in response to the determined relative positions of corneal reflection and the pupil centre in the recorded image. Although the adaptive repositioning of the marker provides for a method and system that is somewhat more complex than the known system and method which uses fixed markers the advantages are significant.

In embodiments the system comprises a display device and the position of the marker is related to the display device.

There are several ways of relating the position of the marker to a display device (for instance a TV or monitor). One way is to shine a marker on a display screen of the display device, on a transparent screen placed in front of the display screen, or, in preferred embodiments, the means for providing a marker and the display device are integrated into a single device.

The display device itself in embodiments comprises a means for providing a marker in an image on a display screen of the display device.

This can, for instance, be accomplished by hiding a marker in the displayed visible image. Hiding, meaning that the marker is indistinguishable to an observer, can be done by providing to the marker a temporal or spatial or combined temporal and spatial signature and/or spectral signature such that a camera tuned to said signature is capable of detecting the marker, while the observer is not.

An unnoticeable marker can be provided by using a marker in a part of the light spectrum outside the human range. The marker is then invisible to the human eye. Infrared (IR) markers and ultraviolet (UV) markers are examples of such markers.

Even a marker in the visible range can be made undetectable to an observer if it cannot be seen by an observer. For instance, a marker can be provided by forming a sequence of images wherein the marker is hidden for a human or animal eye, but is distinguishable to a camera tuned to the marker, In such an embodiment the marker has a temporal signature.

In embodiments the marker is detectable to the human eye.

In embodiments it can be advantageous to provide a human observer or a third person with directly visible information on the gaze direction.

In many instances it is preferred, however, that the marker is unnoticeable to the observer, to avoid an oscillatory behaviour. If the marker is noticed, the observer's eyes may try to track the marker, this is difficult to avoid since an observer's gaze may be drawn to the marker. Since the moving marker is following the eye movement, via the feedback of the system, and the eye may be, without the observer knowing it, trying to follow the marker, an oscillatory behaviour could ensue. If needed, such oscillatory behaviour, however, can be suppressed by introducing an indirect coupling between the measured point of gaze (POG) and the visibly displayed POG (typically a mouse cursor). Such indirect coupling can be achieved by various methods known in the field of control engineering. An example of a linear solution is the use of a proportional integral derivative (PID) element in the control loop. An example of a non-linear solution is the use of a dead-zone, to create hysteresis between the measured and displayed POG.

The display device and the means for providing a marker may be integrated into a single device as stated above. Integrating the display device and the means for providing a marker into a single device has the advantage that the match between the visible information and the marker is accurately known.

A preferred example is a system comprising a Liquid Crystal Display (LCD) which has an IR backlight and a visible light backlight. The LCD device is then capable of providing both a visible image as well as an invisible IR marker on the display screen. Another example is a system comprising a multi-primary display device. Such devices are also capable of providing a marker in an image displayed on the display screen.

The display device is, in embodiments, an image projecting device.

Alternatively the display device and the means for providing a marker can be separate. The means for providing a marker can, for instance, be formed by a transparent shield positioned in front of an image screen of the display device. Within the shield a marker is generated or on the shield a marker is projected by means of a projector. In preferred embodiments wherein a transparent shield is used in front of a display screen the transparent shield is provided with means for determining the positioning of the shield with respect to the display screen of the display device.

The marker can also be projected directly on a display screen. Using separate devices has the advantage that a standard display device can be used within the system without many further adjustments.

In other embodiments the system comprises a means to provide the marker and establish the position of the marker, and reposition the marker directly on a scene or in or on transparent plate in front of a scene. In such embodiments the system does not comprise a display device. Such a system is, for instance, useful for monitoring the focal attention of a person driving a car or truck. For instance, in a preferred embodiment, the transparent plate is a windshield of a vehicle and on the inside of the windshield on inside the windshield an invisible IR marker is generated, thereby maintaining an unobstructed view outward towards the road ahead. The gaze of the driver is tracked and, if the tracking shows that the driver is in danger of falling asleep or loosing attention, a warning signal is given to alert the driver.

Projecting a marker on a scene can for instance be advantageously used to track the gaze of an observer through a shop window onto displayed goods.

In embodiments, the system comprises means to provide more than one marker and means to identify the markers and couple the markers to one or more eyes of observers. The advantage of this embodiment of the system is that the latency only increases as the number of simultaneously tracked observers increases.

BRIEF DESCRIPTION OF THE DRAWINGS

These and other objects and advantageous aspects will become apparent from exemplary embodiments that will be described using the following Figs.

The figures are not drawn to scale. Generally, identical components are denoted by the same reference numerals in the figures.

DETAILED DESCRIPTION OF PREFERRED EMBODIMENTS

Figure 1:
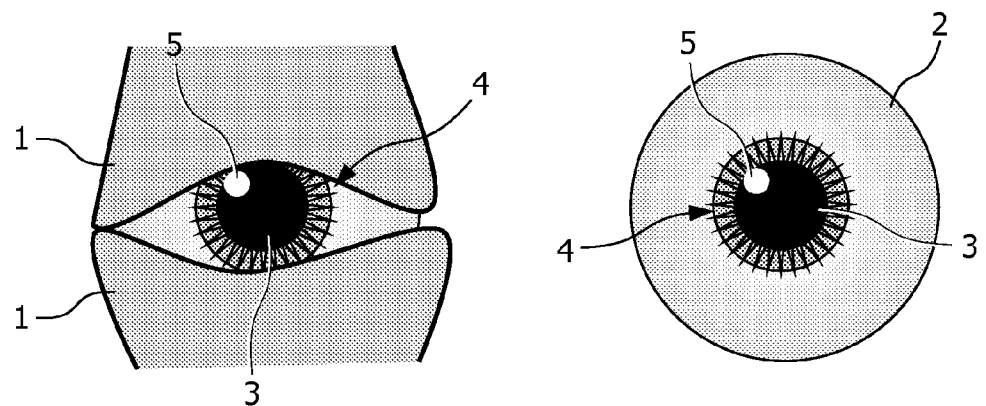
FIG. 1 illustrates the effect of specular light reflection.

FIG. 1 illustrates the effect of specular light reflection. The eye lids 1 surround the eye ball 2. The iris 4 comprises a pupil 3. The corneal reflection of a light source is schematically indicated by 5.

Figure 2:
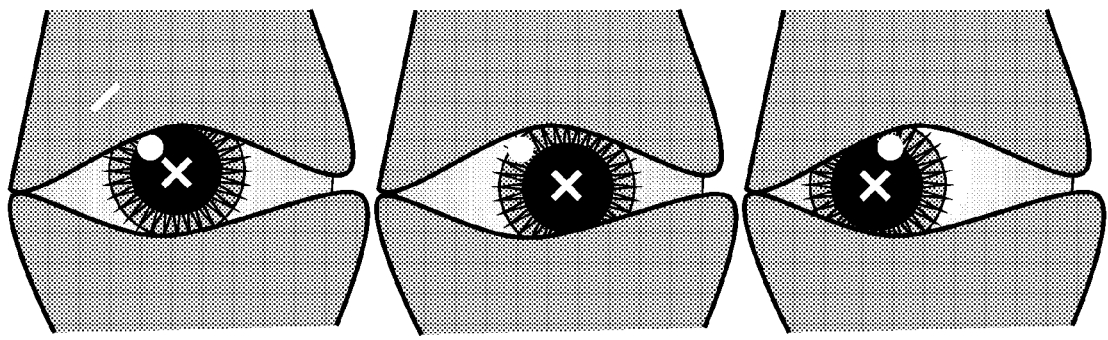
FIG. 2 illustrates the stationary reflection of a fixed light source when moving the eye.

FIG. 2 illustrates the corneal reflection, or 'glint', is resulting from a fixed light source, it has a tendency to roughly maintain a fixed position as the eyeball rotates, changing gaze direction. The reflection of the fixed light source tends to maintain a fixed position when the eyeball rotates to change gaze direction. The 'x'—mark indicates the shifting centre of the pupil as the person changes gaze direction.

Figure 3:
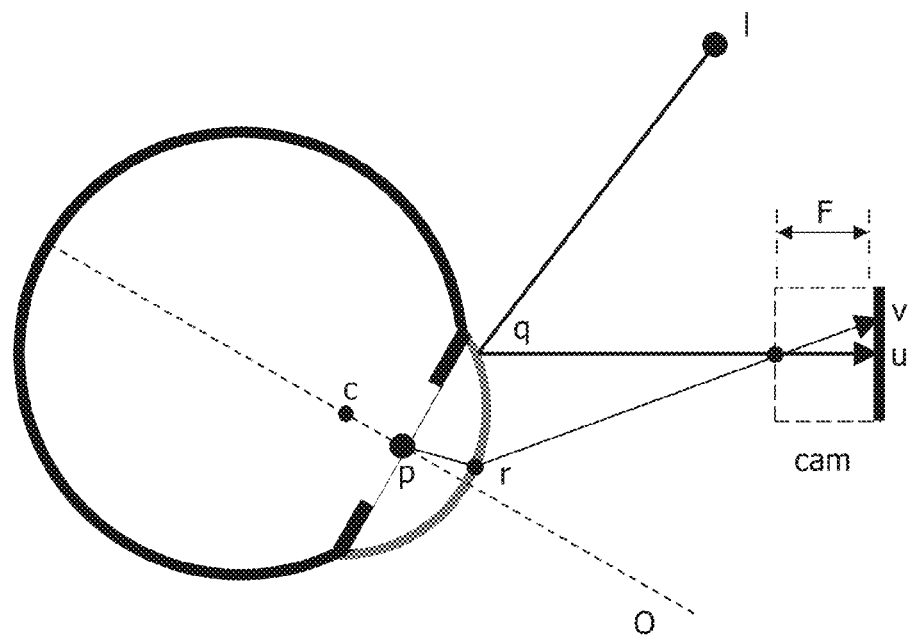
FIG. 3 illustrates a basic gaze tracking configuration

This relative stable 'rotation invariant' glint position forms the basis of virtually all commercially available gaze tracking systems that use video and for instance an IR light source. The diagram in FIG. 3 shows how the projection of the glint and the pupil centre can be found by construction of the associated light rays. Cam indicates the camera, l the light source, c the corneal centres, p the pupil centre, r the refraction of the pupil centre, q the reflection of the lights source, F the focal distance of the camera, v the image of the pupil centre in the camera, u the image of the corneal reflection of light source 1 in the camera CAM.

Figure 4:
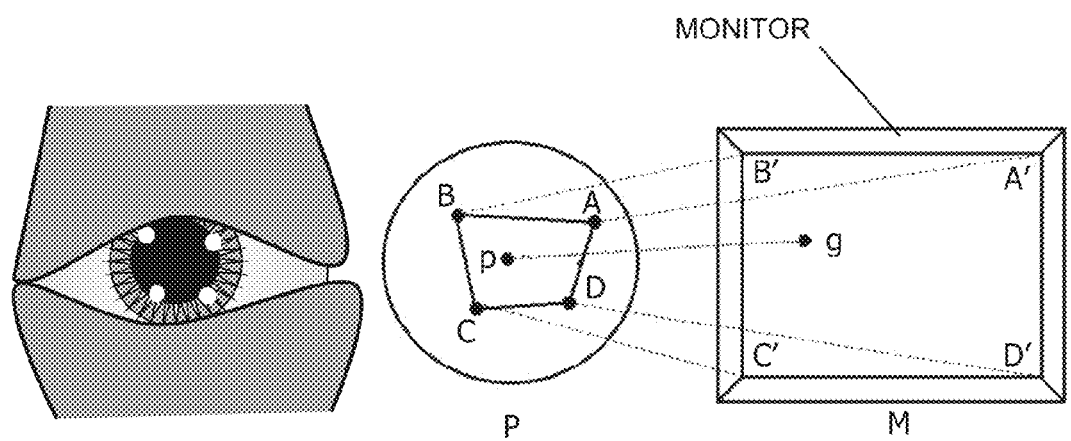
FIG. 4 illustrates a typical video frame of a current gaze tracking system

The estimated gaze direction, here represented by the optical axis o, is based on assessment of the captured pupil centre against one or multiple glint positions. As the pupil essentially is a uniform circular disk, some image processing is required to recover the pupil centre from the, generally elliptic, projection of the pupil disk. Note that refraction occurs at the interface between air and the aqueous domain in the eye. In FIG. 4, a video frame is shown of an eye observed with a normal camera. The four glints A, B, C and D on pupil P are reflections of four IR LEDs A', B', C' and D' on the corner of a display. The estimated gaze direction g on the monitor M is indicated in FIG. 4.

The accuracy with which the gaze direction g can be recovered with this approach is relatively high. However, the method has major disadvantages:

Calibration is required to translate the position of the pupil centre, relative to each glint position, into a gaze direction or a point-of-gaze on a display screen.

As the relationship between the point-of-gaze and this relative pupil position assumes stationary light sources, the tracker becomes very sensitive to changes in head position.

Calibration is required for each new individual to deal with small differences in physiology (corneal surface curvature, placement of the pupil along the optical axis).

Figure 5:
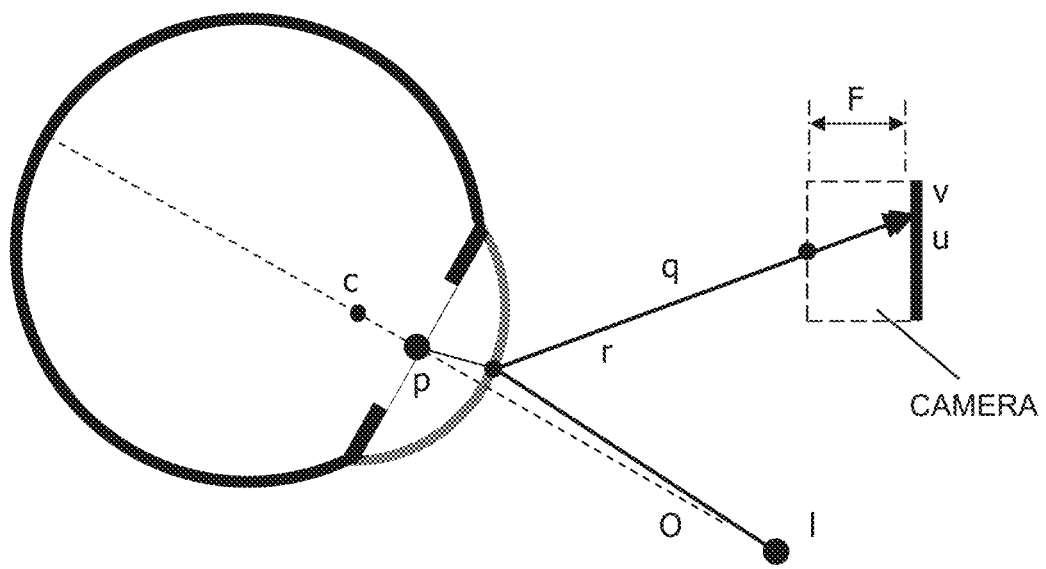
FIG. 5 illustrates coincidence of reflection of marker and pupil centre when observer is looking at the marker.

The relationship between the projection of the pupil centre and the light reflection holds a remarkable property. In the situation that the eye is gazing at a light source, its reflection in the cornea appears to coincide with the pupil centre. This situation is sketched in FIG. 5. Note that this literal 'coincidence' of glint and pupil-centre is not a trivial situation. The value of the eye's refractive index and the placement of pupil behind the corneal surface happen to cause this fortunate optical phenomenon.

To some extent this is used in the system and method of US 2006/0110008. The known system uses a relatively large number of markers to find a marker that is within a threshold distance of the pupil centre.

The known system and method however has a number of shortcomings:

The known system uses temporal light modulation to encode the different identifiers introduces a latency (expressed in number of frames) that is proportional to the code length.

The accuracy is determined by the threshold distance. Either one has to make the threshold distance small for high accuracy, which requires a large number of markers and thus a large temporal latency, or one accepts a relatively large threshold distance, to reduce the temporal latency, but that the accuracy of determining the gaze direction is compromised.

Figure 6:
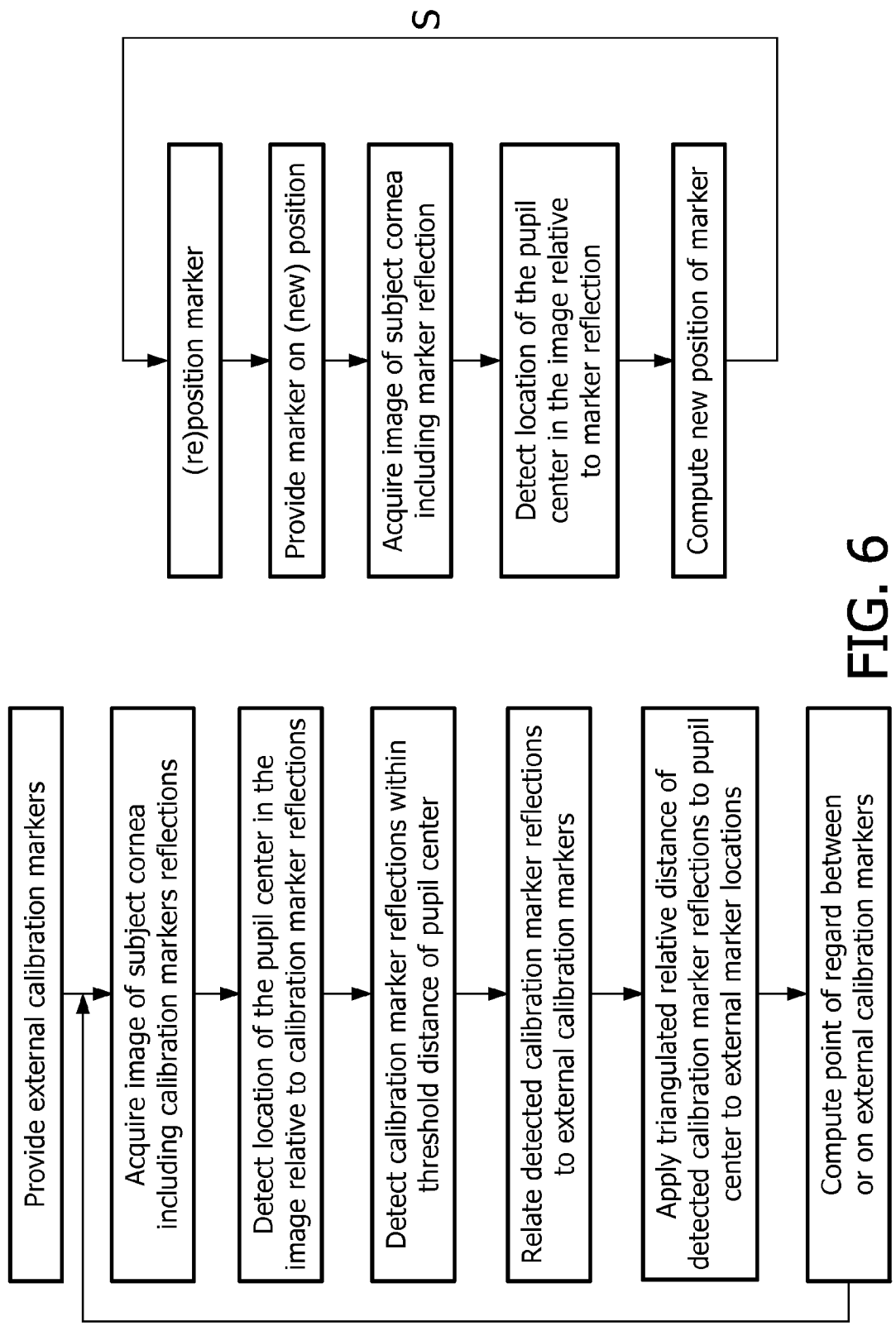
FIG. 6 illustrates the difference between the method of US 2006/011008 and the method of the invention.

FIG. 6 illustrates the difference between the system and method of US 2006/0110008 and the system and method of the invention, wherein the left hand scheme illustrates the know system and method, and the right hand scheme the system and method in accordance with the invention.

In the known system and method, the markers form a fixed pattern covering the field of gaze. In the known system, schematically illustrated on the left hand side of FIG. 6, temporal modulation is used to label each separate IR-marker or marker group by using temporal modulation, e.g. by using temporal binary encoding. This means that, in order to binary encode n different IR-markers or marker groups, a code length at least m=log 2(n) bits is necessary. Consequently, m video frames are necessary to identify all encoded IR-markers or marker groups.

There are several disadvantages:

Tracking of the gaze over, e.g., 16×16 uniquely labelled IR-markers requires the identification of 256 different encoded labels, such that already a latency of 8 frames is required for a relatively coarse gaze estimate. The finer the gaze estimate, the more markers must be used, and the larger the temporal latency becomes.

Given the motility of the eye, temporal latency quickly gives rise to motion artefacts.

In the application to eye-guided cursor control, the response of the gaze tracker should be instant, with minimal latency.

The system and method of the invention, schematically shown on the right hand side of FIG. 6, differs from the known system and method in that the position of the light source(s) is not fixed but dynamically adjustable. To establish 'glint-pupil coincidence' a movable marker is used, such that the reflection of the dynamically movable marker is kept at the centre of the pupil by a control mechanism. The relative positions of the pupil centre and the marker reflections are detected. From the relative positions of the pupil centre and the corneal reflection of the marker a new position of the marker is computed. The new position is computed to have the corneal reflection of the marker coincide with the pupil centre. This is schematically indicated in FIG. 6 by a repositioning signal S. Using the repositioning signal S the marker is repositioned. It is remarked that 'repositioning signal' can be any data in any form by which the marker can be repositioned. The result of re-positioning is that the gaze direction is always along the line or at least very close to a momentary position of the marker. Because the position of the marker is continuously moved to make its reflection coincide with the pupil centre, the physical position of the marker is updated to coincide with the point-of-gaze. When the feedback loop is properly closed, the system continuously provides the coordinates of the point-of-gaze, which are identical or at least very close to the coordinates of the marker.

Figure 7:
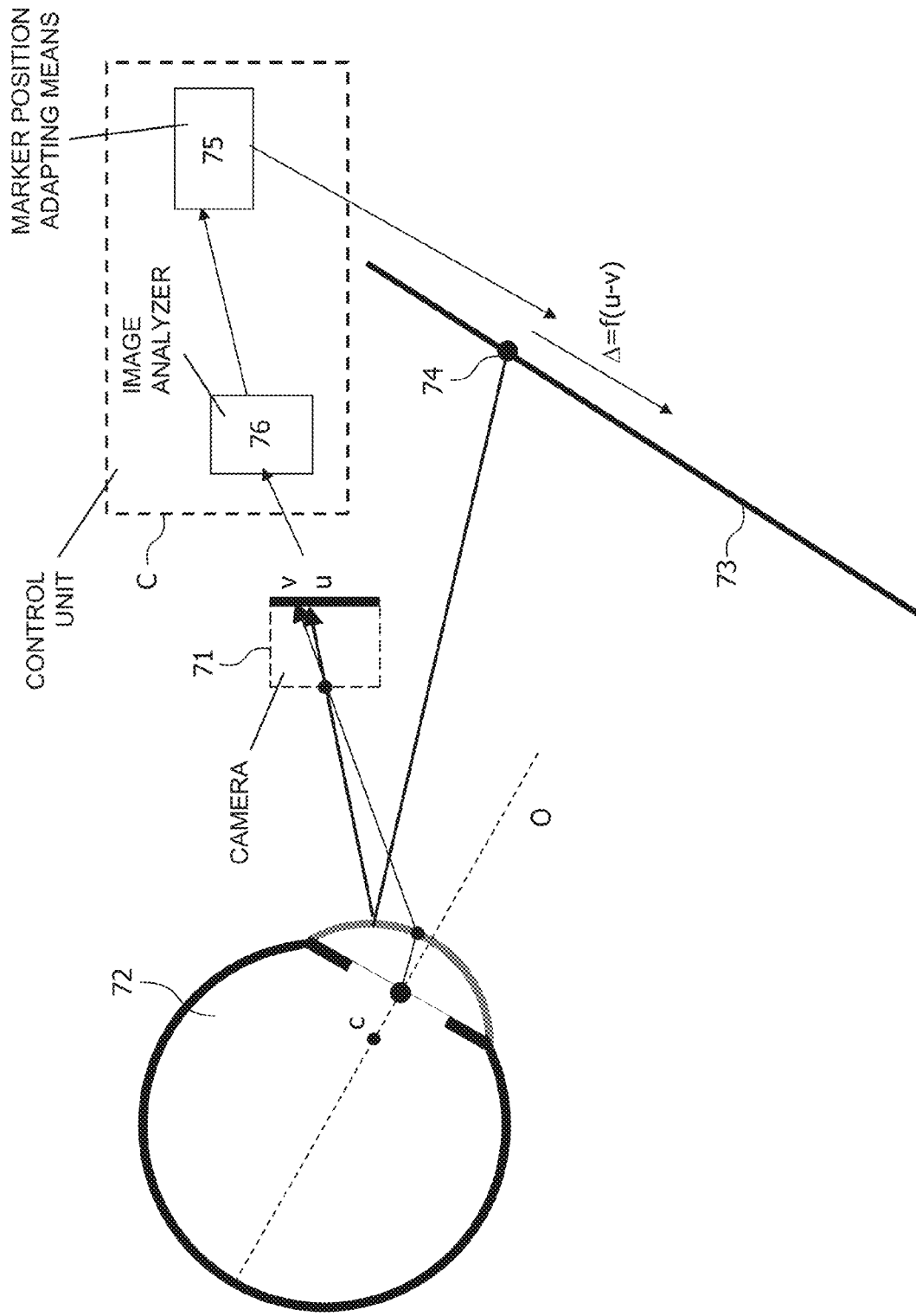
FIG. 7 illustrates a system of the invention
Figure 8A:
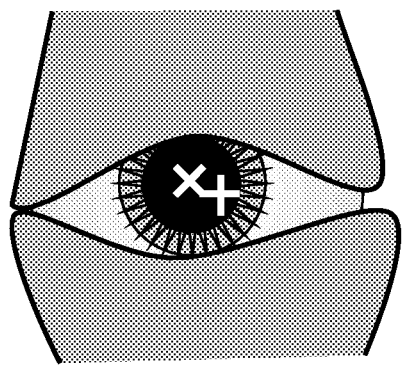
FIG. 8 illustrates the basic principle of the marker movement on the basis of feedback.
Figure 8A:
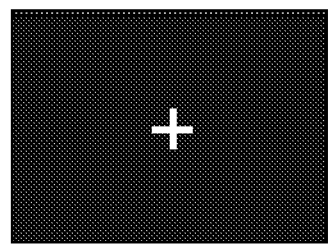
Figure 8B:
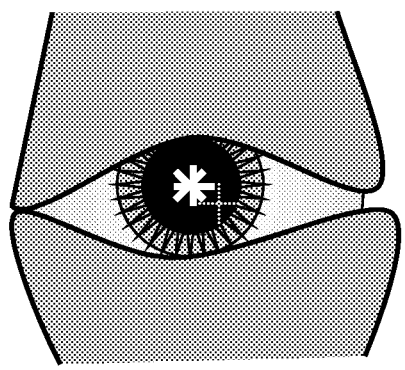
Figure 8B:
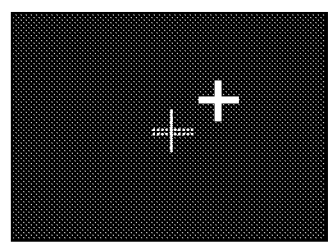
Figure 8C:
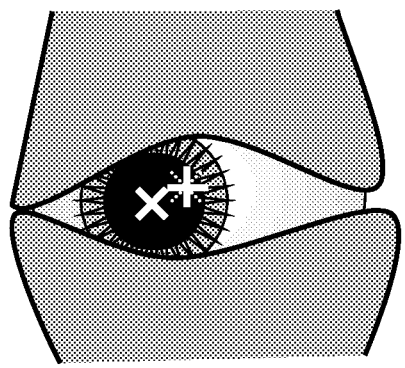
Figure 8C:
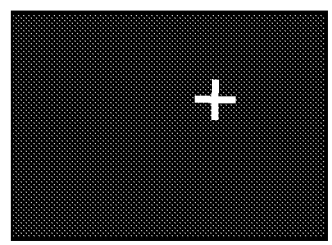
Figure 8D:
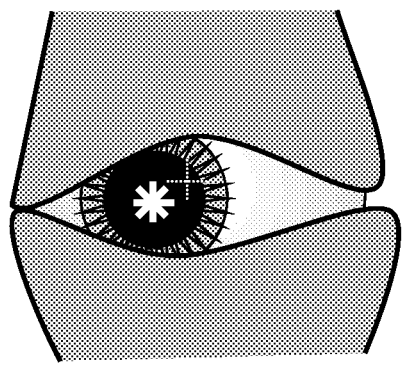
Figure 8D:
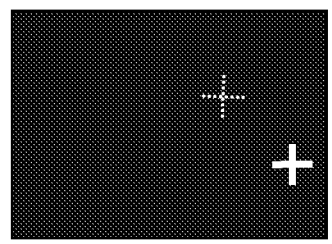

FIG. 7 illustrates a system in accordance with the method. The system comprises a camera 71 (or more in general: a means to obtain an image). The camera in operation records an image of an eye 72 of an observer. The system comprises a means 73 for providing a movable luminous marker 74 in the field of view of the observer. This light source functions as a marker. The position of the marker within the field of view of the observer can be dynamically adapted. To this end, the system comprises a means for adapting (75) the position of the marker. Within the concept of the invention a light source is any means that produce light rays that can be reflected by the eye. The image data is analysed in an image analyser (76). The image analyser establishes the difference u-v of the corneal reflection of the light source (u) and the pupil centre (v), i.e. data on the relative positions of the pupil centre and the corneal reflection of the marker. Either the analyser directly calculates the data for repositioning the marker or the analyser provides data for the relative position of the reflection of the marker and the pupil centre and a further analyser provides, based on the data on the relative positions, data for repositioning the marker. This data (or data derived form this data) may be in the form of a repositioning signal, i.e. a signal that is, further down the chain of the system, used for repositioning the marker. The signal is sent to the means (75) for adapting the position of the marker (74) to reduce the distance between the corneal reflection and the centre pupil. The analysing means and the means to adapt can be combined in a control unit C. The shift A, i.e. the repositioning, that the marker 74 makes is a function of the difference u-v in the recorded image. The image produced after repositioning of the marker is again analysed and the process of adapting the position of the marker is repeated, if need be, until the corneal reflection of the marker coincides, within reasonable accuracy, with the centre pupil. In this example a single marker 74 is shown; within the concept of the invention more than one movable marker can be used to simultaneously track the gaze of several observers. The corneal reflection is the reflection on the outer surface of the lens of the observer. In case the observer wears a contact lens, the outer surface of the contact lens is considered to form the outer surface of the lens of the observer.

The invention is based on the insight that it is advantageous to establish a connection between the position of the marker and the point-of-gaze by way of a feedback control system. A control system adjusts the marker position until its reflection in the cornea coincides or nearly coincides with the pupil centre. The difference between the position of the corneal reflection and the centre of the pupil forms or is at the basis of a feedback signal that is used to reposition the marker.

It has been found that the temporal latency of a system according to the invention is much smaller than that of the known system. Also, it is more accurate since there is no fixed threshold value. Instead of fixed marker positions the position of the marker is adjusted in dependence of a feedback signal derived from a measurement of the relative positions of the corneal reflection of the marker and the pupil centre.

In the system and method of the invention, latency is reduced as the marker is allowed to move to coincide with the pupil centre. The basic principle of the marker movement on the basis of feedback is illustrated in FIG. 8. This figure shows the eye and an IR 'display' during a sequence of events. Note that the display pattern is mirrored with respect to the reflected pattern. The pupil centre is given by a "×", the corneal reflection of the marker by a "+".

Part A illustrates an IR-marker at an initial position; the pupil also starts at an initial position.

In part B the IR-marker is moved until its corneal reflection coincides with the pupil centre (from the dotted '+' to the solid '+').

In part C the observer changes gaze direction, and the pupil adopts a new position (from the dotted '×' to the solid '×'). In part D the IR-marker is again moved to maintain its corneal reflection to match the pupil centre, again directly indicating the gaze direction.

The invention can be used in a wide variety of embodiments. Below, some non-restrictive examples are given.

In many of the examples the marker will, for simplicity sake, be described as an infrared (IR) marker. Although the use of IR markers form preferred embodiments it is explicitly stated that other types of luminous markers, such as UV markers, or markers in the visible light region, can be used.

The system has a control system that contains:
  a position-comparing operation (in FIG. 7 shown as an analyzing means) that compares the position of the corneal light reflection of the marker, for instance an IR marker, with the apparent position of the pupil centre;
  a position-calculation operation that calculates a new position of the IR marker, or the difference between the present position and the ideal position with the aim that the new or adjusted position causes the IR marker reflection and the apparent pupil-centre position to coincide followed by;
  an adaptation of the position of the marker in accordance with the newly calculated position;

Data to adapt the position are also called "repositioning signal".

It is remarked that within the method and system a feedback loop is used, so an initially less than ideal position calculation will have the effect that the reflection of the marker, after repositioning, will come closer to the pupil centre but not in the most effective manner. A following calculation step will then be taken to improve coincidence. In preferred embodiments the parameters of the position-calculation operation are adjustable to fine tune the calculation to improve the accuracy so that as few as possible iterative steps are necessary. This will improve the speed of calculations, and thereby reduce the latency of the feedback loop. Calculations can be performed step by step or in a single operation.

Figure 9:
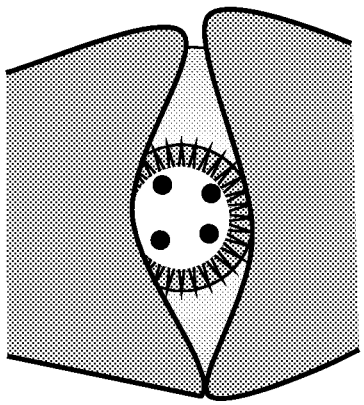
FIG. 9 illustrates a method for finding the centre of the pupil.
Figure 9:
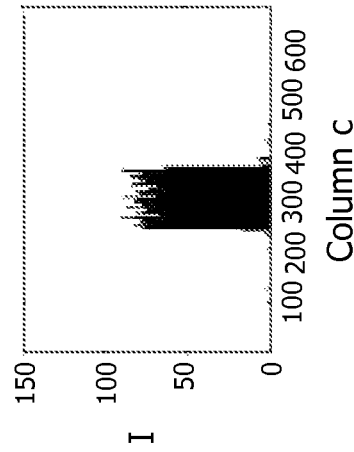
Figure 9:
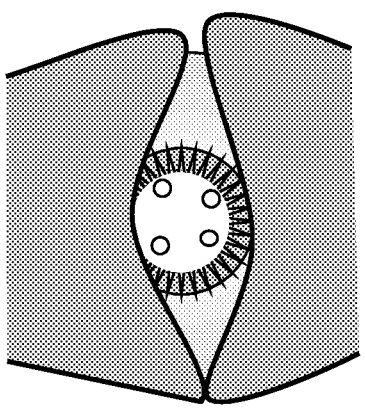
Figure 9:
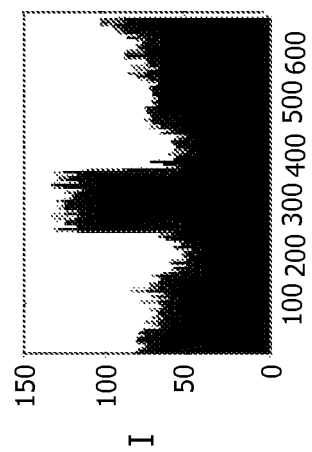
Figure 9:
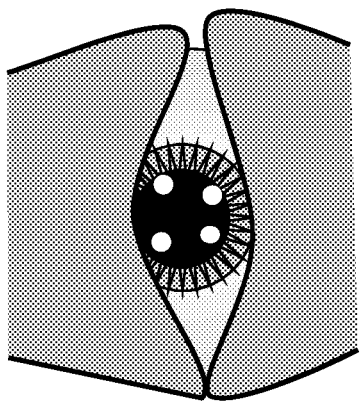
Figure 9:
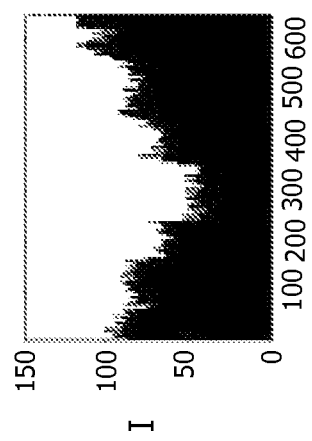

FIG. 9 illustrates a method for finding the centre of the pupil. Segmentation of the pupil can be aided by the use of light sources near the camera, positioned as close as possible to the optical axis of the camera. Although this solution is not new and widely applied in conventional gaze tracking, it can also be used in the new proposed system.

When this 'coaxial illumination' is active, an IR 'red-eye' effect is created which causes the retina to light up in the pupil, as shown in FIG. 9. The pupil disk follows from the difference between two images, one with and one without coaxial illumination.

FIG. 9 shows schematically a captured eye image with intensity profile of a single line view with a) illumination by non-coaxial sources; b) illumination by coaxial source; c) difference image, b minus a. Estimation of the pupil centre can be performed by a great variety of algorithms, the cheapest of which is to calculate the centre of mass of the projection of the pupil disk.

The invention can be embodied in various ways in various systems.

The system can comprise a display device and a means to provide a marker on the display. The means to provide a marker on the display can be integrated into the display device. The means to provide a marker can also be separate from the display device. An example of an integrated device is one in which the display device provides both the image as well as the marker. An example of a separate marker providing means is a device which projects a marker on a display screen or a device which comprises a separate transparent shield put in front of a display screen in which shield an IR marker can be generated.

Figure 10:
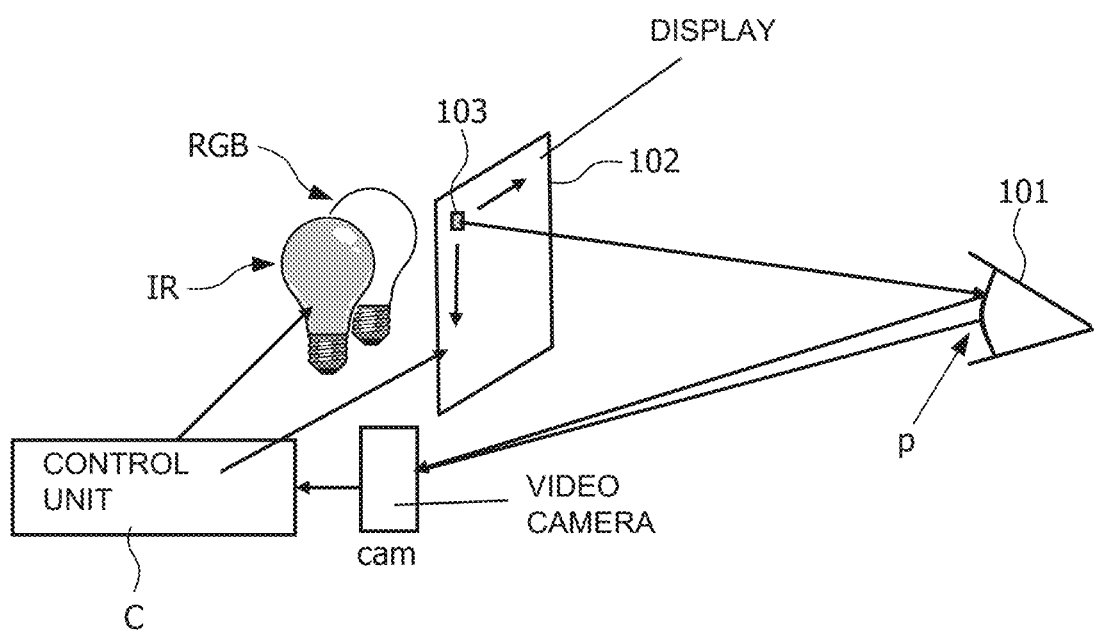
FIG. 10 illustrates an example of a system in accordance with the invention.
Figure 11:
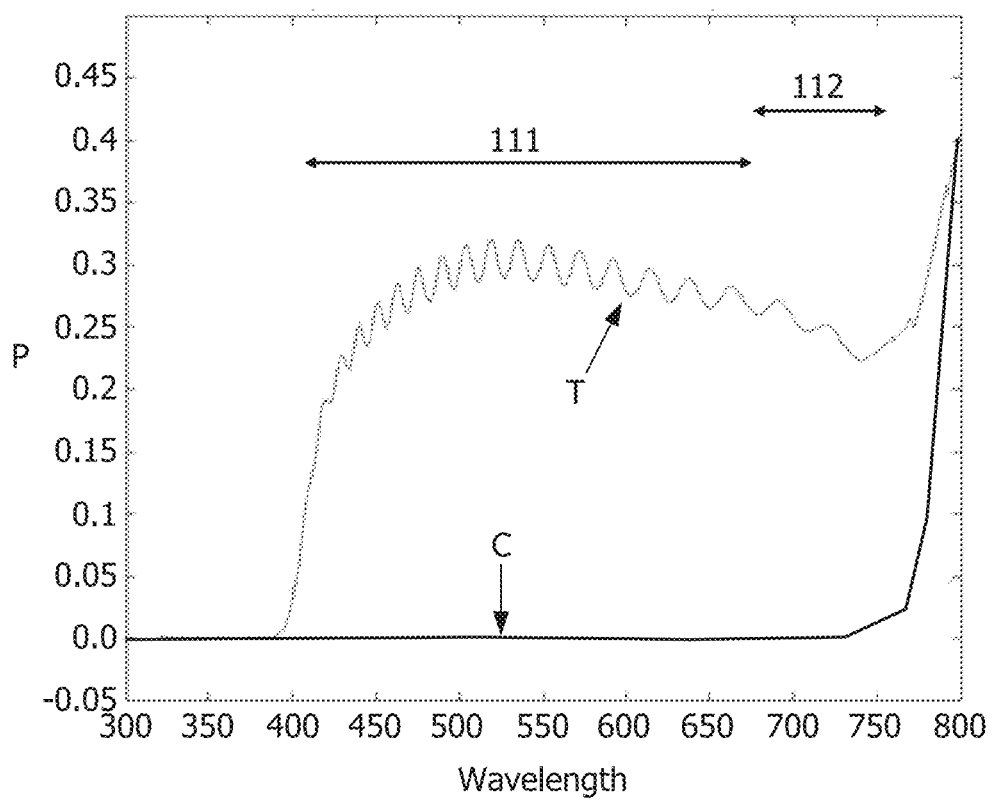
FIG. 11 illustrates the relative power of the transmission T of a commonly used LC material in the visible light region 101 and the near IR region 102 as a function of wavelength.

FIG. 10 illustrates an example of a system in accordance with the invention. A first embodiment is based on the use of an LCD display 102 which has an IR backlight (IR) in addition to the normal visible backlight (RGB) as depicted in FIG. 10. The implementation and control of the system, using control unit C is in principle similar to that of scanning-backlight LCD systems and particularly of colour-sequential LCD systems. The video camera (cam) is synchronised with the backlighting system. The synchronization causes the backlight to alternate between IR and visible light. During the visible-light phase the normal image is shown. During the IR phase the LCD panel 102 displays a pattern that serves as the movable IR marker 103; during this phase the camera (CAM) captures an image of the eye 101 with the reflected marker. The centre of the pupil can be obtained using the method discussed earlier, e.g. during the visible-light phase. Experiments have shown that LC material is capable of modulating near-IR light just as it modulates visible light. FIG. 11 illustrates the relative power of the transmission T of a commonly used LC material in the visible light region 111 and the near IR region 112 as a function of wavelength. The transmission curve T for the LC material in the open state is such that visible light as well as near IR light is transmitted. In the closed state, as illustrated by curve C, visible light as well as IR light is not transmitted. The transmission FIG. 11 shows that an LC display is capable of modulating IR light and thus to create a moving IR marker. The IR light source can also be lit continuously since the human eye does not see much of the near IR light anyway. Synchronization is however preferred since this provides a possibility to more easily distinguish IR light from the IR marker source from other spurious IR light reflections.

The camera CAM records the image, the control system C (or a calculator within the camera cam) calculates the difference between the corneal reflection of the IR marker and the centre of the pupil, it is calculated to which position on the LCD display the IR marker has to move to coincide with the pupil centre, the IR marker is repositioned, and the process is repeated, if needed. In this example the means to provide a marker are to a high degree integrated into the display device.

A second embodiment of IR-marker superposition is to use spatially segmented IR backlight in addition to the visible backlight. By choosing the IR light wavelength sufficient far from the visible range, it has been found that the LC material becomes transparent to the IR light, regardless the open or closed state of the pixels. The advantage is that the visible backlight can stay active and the LC panel can be used exclusively for the normal visible image. Now, the resolution of the IR marker is that of the segmented IR backlight. The segmented IR backlight is controlled to control the position of the IR marker. In this example the means to provide a marker are also integrated into the display means, but to a lesser degree than in the first example. Alternatively the means to provide a marker can be formed by a projector which projects an IR beam, via a system of movable mirrors on the LC display device. In this example the means to provide a marker are much more separated from the display device.

Going yet one step further would be to provide a transparent plate on which a movable IR marker is provided. This can be done for instance by projecting a marker on a transparent screen. The image for the viewer is then the field of view through the transparent plate.

Starting from the LCD display a marker can also be provided in the following manner:

An image is displayed in accordance with the image information as provided to the display. At the position of the marker the intensity (or for instance the intensity of one of the colours) is reduced by a slight amount. In the next frame the intensity at the position of the marker is increased by the same amount. If this adding and subtraction of intensity is performed at a high enough frequency, the human eye cannot perceive any flickering due to the changes in intensity. However, a camera synchronized to the marker frequency can, by subtracting two sequential images, find the position of the marker. The advantage of this embodiment is that it can be used in and for any existing display device, providing that the display device has a high enough image frequency. Most modern devices are capable of performing such feat. It is not needed to provide an IR source to provide an IR marker. In this embodiment the marker is hidden in the visible signal, indistinguishable to an observer but distinguishable to a camera tuned to the temporal signature of the marker. The disadvantage is that at parts of the screen that are nearly black, it could be difficult to add and subtract intensity. However, the human eye tends to gaze at those parts of the screen with the highest or at least high intensity anyway. The fact that at least two frames are needed to find the marker is a disadvantage, but displays are being provided with ever higher image frequencies. Alternatively the marker may be provided with a spatial signature that is not noticeable to an observer but is to a camera tuned to the spatial signature.

An alternative method for providing hidden markers using known display devices is possible if the device is capable of making the same colour in two different ways. So called RGB-W display devices are known. Such display devices comprise red, green and blue pixels as well as white pixels. This allows white areas in the image (or in fact within a large range of colours) to be made in two different manners. The simplest example is a device in which a white area can be made by a combination of red, green and blue pixels as well as by white pixels. To the human eye the difference between "RGB"-white areas and "white"-white areas is invisible. However, in the IR and/or UV regions or in a particular region of the visible light spectrum the difference is detectable. The display itself is not changed and the displayed information is also not changed. However, by using the possibility that white light can be made in two different ways it is possible to provide in the image a marker that is visible to a camera, for instance an IR or UV camera or a visible light camera with a colour filter in front of it, but invisible to the observer. The marker is then distinguishable by its spectral signature, signature meaning distinctive feature. This embodiment can for instance be advantageously used for tracking the gaze of a human observer reading a text. Texts are composed of relatively small black letters on a white background. Also one can track the human eye following an animated figure on a white background. The same type of method can be used for any device that is capable of providing a colour in two different manners. Examples are for instance the so-called spectrum sequential displays, also referred to as a hybrid spatio-temporal color displays. These displays combine the conventional LCDs and color sequential LCDs. Such a display conventionally has addressable elements with two (broadband) color filters (e.g. magenta and cyan) and two types of backlight color fields (e.g. cyan and yellow) although other combinations of color fields and color filters can be used such as for instance:

(1) magenta and cyan color filters with yellow and blue color fields, and
(2) magenta and green color filters with yellow and cyan color fields.

Figure 12:
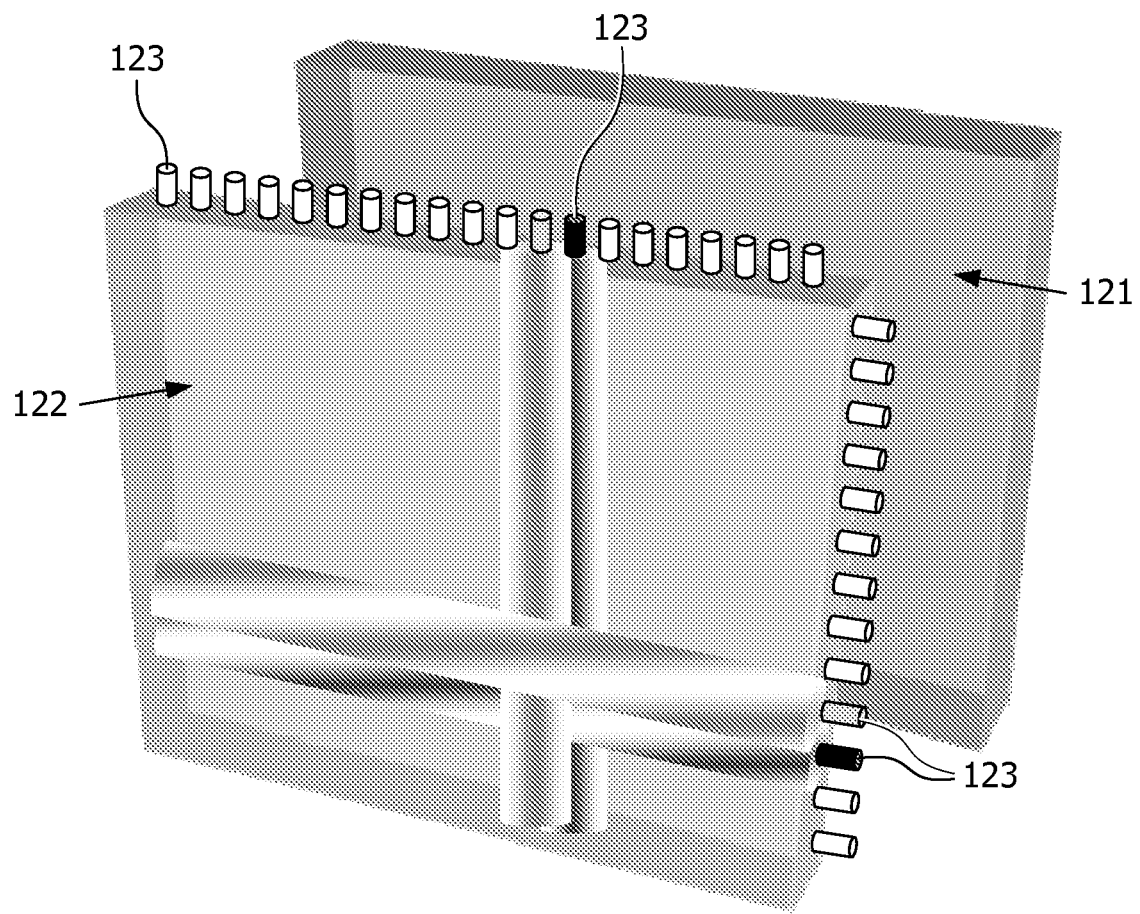
FIG. 12 illustrates a further embodiment based on the use of a light-guiding diffuser plate, placed in front of a display and illuminated by peripheral segmented IR illumination.

A further embodiment is based on the use of a light-guiding diffuser plate, which is placed in front of the display and illuminated by peripheral segmented IR illumination. This embodiment is illustrated in FIG. 12. A light-guiding diffuser plate 122 is used, which is placed in front of the display 121 and illuminated by peripheral segmented IR illumination devices 123. The transparent diffusing light guide 122 acts a means to create an invisible IR marker without obstructing the free view to the image, display or scene behind it. By using a marker that covers at least two peripheral IR illumination devices 123, and by gradual varying the mutual intensity as the IR marker shifts in position, the centre of the marker can be recovered at a resolution which is smaller than the distance between the devices 123. Thus the number of devices 123 can be relatively small while yet providing a high resolution.

Figure 13:
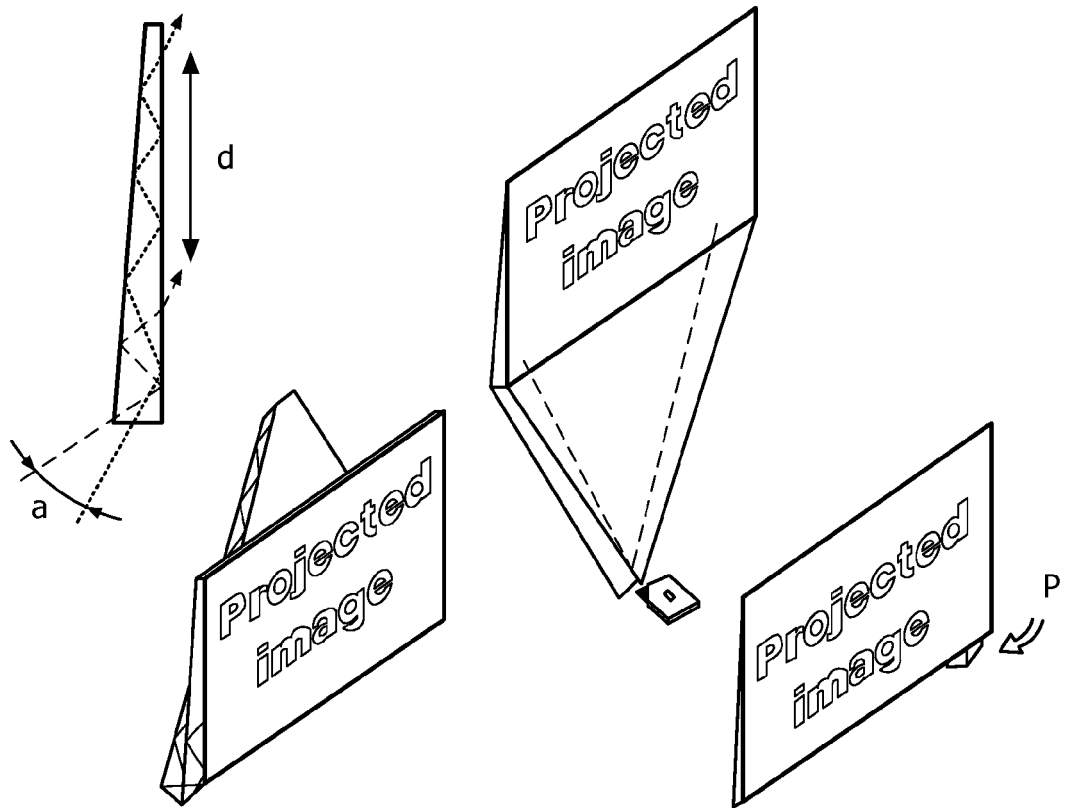
FIG. 13 illustrates a system comprising a Wedge display.

A variation on this embodiment is based on the use of a Wedge display. A Wedge display comprises essentially a light guide that transfers a focused light field from a projector to a projection screen on the basis of consecutive internal reflections such that the geometric integrity of the light rays is preserved. FIG. 13 illustrates such a device.

FIG. 13 shows that the light guide can be transparent as the projected light is confined by internal reflection. The lightfield finally escapes the guide as the rays cross the material interface at less than the critical angle. In absence of a frontal diffuser and back cover, this technology is suitable to create a translucent display that allows a free view on the display or scene behind.

In a further embodiment IR illumination is achieved by conversion of UV and/or visible light into infrared light using fluorescence. The aim is to obtain an efficient way to generate IR light, in (typically outdoor) situations where the ambient IR light deteriorates the legibility of the IR-marker(s) by the camera system. In increasingly brighter daylight, the emitted light from the IR-marker increases in strength. The fluorescent IR light source can be considered as a continuous backlight, such that local or global shutters can be used to modulate its intensity. A range of fluorescent pigments is known that can give a large variety of (transparent) plastics a fluorescent property. In this product range, there are also pigments available that convert any visible light into IR light. The pigment is for instance used in industrial applications such as laser-welding of transparent plastics. Application of such pigments as a passive IR illuminator in the context of gaze tracking is not known.

In a further embodiment the IR marker is projected by a projector (essentially a beamer) which only emits IR light invisible to the user. The IR marker is a focused image that is either projected on a normal visual display, or on a sufficiently diffusing transparent screen allowing a transparent view on the scene behind, or on the scene itself.

In a further embodiment the IR marker image and a normal visual image are generated by two separate displays of which the images are superimposed using a semitransparent mirror, using the classical teleprompter or autocue configuration.

FIG. 12 illustrated that the marker need not be a point. A marker is any point, area or pattern that can be distinguished as remarkable. It can be a point, a circle, a cross-hair or another pattern.

A number of ways of making a marker are described above and below. Where "IR-marker" is mentioned below, it is to be recognized that a marker can also be in the visible range, or in the UV range. "IR-marker" is used below given the fact that for many embodiments, the use of an IR marker is preferred. However, it does not form a restriction for the invention in a broader sense.

The shape of the IR marker is preferably such that its reflection in the eye is readily captured by a camera and readily detected by computer vision algorithms for the goal of position tracking. Yet, the shape of an IR-marker can be limited by the way the marker is generated and superimposed on the visible image.

An embodiment of a feedback-based gaze tracking system would be based on a point-shaped marker, of which the reflection becomes a point-shaped glint on the cornea. Although most current gaze tracking systems rely on point-shaped IR sources, the accuracy of position estimation on the basis of their reflection is quickly governed by the sensor resolution.

The marker is preferably comprised of a connected shape, i.e. a pattern.

Figure 14:
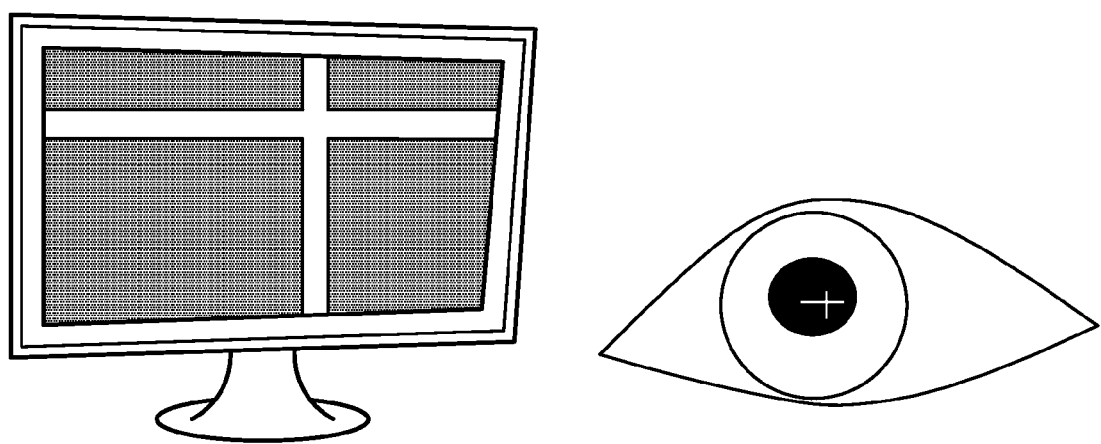
FIG. 14 shows how a marker of pattern, in the example a cross, is visible as a reflection in the eye.

An embodiment of a connected shape is already shown in FIG. 12. A connected shape embodiment is, in the example of FIG. 12, based on the use of a cross ('+') shaped pattern consisting of two intersecting lines that each span the whole width or height of the target display. In this case the point of gaze is associated with the intersection point of the two lines. An advantage of the cross pattern is that it can be generated using peripheral illumination as proposed in the embodiment of FIG. 12 above. In FIG. 14 is shown how such a cross is clearly visible as a reflection in the eye. The connectivity of the pattern allows for sub-pixel recovery of the intersection coordinates.

A further embodiment is based on the use of a pseudo-random IR-light pattern that potentially provides more robust detection with a camera system as more simple patterns may give rise to false pattern detections.

Figure 15:
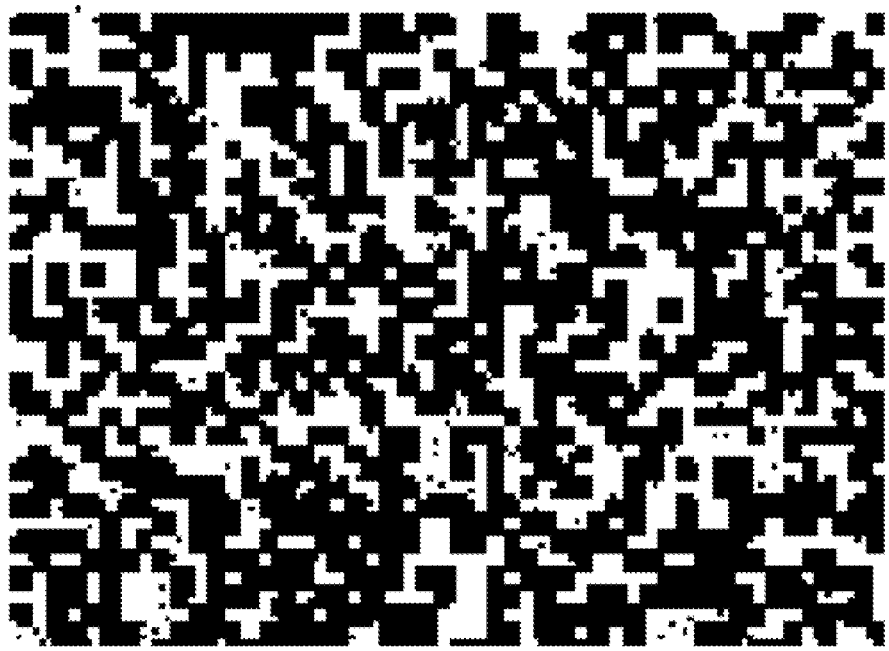
FIG. 15 illustrates a pseudo-random IR-light pattern as a marker

FIG. 15 shows such an example. The pattern seems random, but it is pseudo random. The camera can recognize the pattern and can find a point within the pattern, for instance the centre of gravity. This centre of gravity than provides the position of the 'marker'. A complicated pattern can avoid problems with false pattern recognition. A false pattern recognition can for instance be present when the camera and/or marker recognizing algorithm originally recognises another IR source (for instance the reflection of a lamp) as the IR marker. Such misrecognition can be corrected by checking the result of the change in position of the IR marker, since the true IR marker will move, whereas the 'false' IR marker will not, but in circumstances this can reduce the accuracy or reaction time of the system.

A further embodiment uses a known spatial shift of the IR-target to resolve relationship between the position of the IR-target in the real world and reflected position on the cornea. As we propose a feedback mechanism to control the IR-target position to finally match the point-of-gaze, in absence of a model, the point-of-gaze is typically found in consecutive iterative steps. Each iteration step requires a new-video frame, showing the reflection of a new position of the IR-target. The following method is intended to minimize the number of iterations, and therefore the latency in response. The relation between the coordinates and the reflected position on the cornea is not linear (affine or perspective) transformation, due to the curvature of the cornea.

Figure 16:
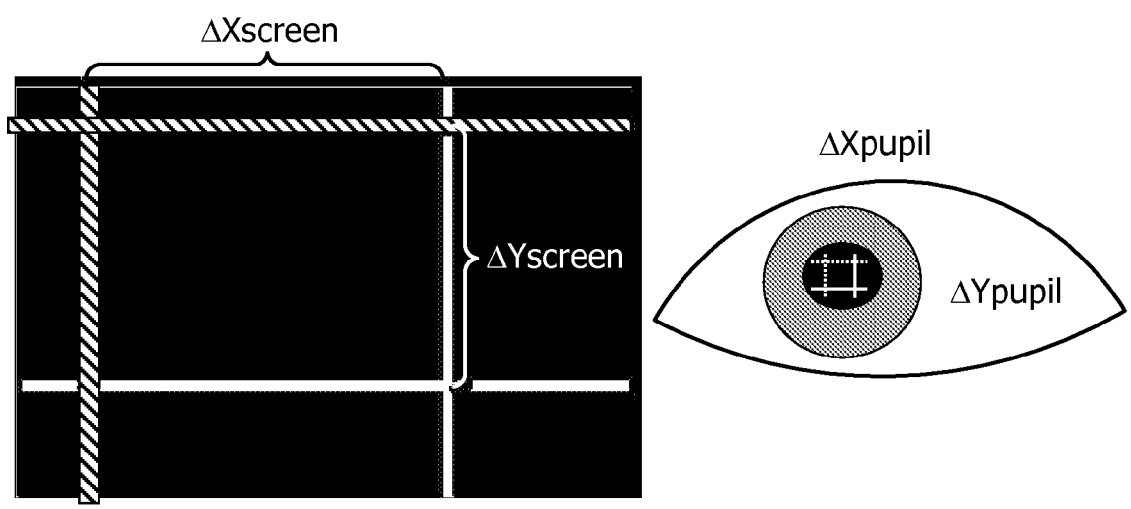
FIG. 16 illustrates the use of two separately acquired IR targets and their appearance on the cornea as a mean to estimate two proportionality constants, that serve as a first-order (linear) approximation of the true relationship.

FIG. 16 below illustrates the use of two separately acquired IR targets and their appearance as reflections on the cornea as a mean to estimate two proportionality constants, that serve as a first-order (linear) approximation of the true relationship.

The two proportionality constants can be defined as $$C_x = \frac{\Delta x_{screen}}{\Delta x_{pupil}} \text{ and } C_y = \frac{\Delta y_{screen}}{\Delta y_{pupil}}.$$

Experiments have shown that an estimation of $C_x$ and $C_y$ on the basis of two consecutive measurements suffice to exactly match the point-of-gaze in the next iteration. By maintaining a history of prior differences and prior values of $C_x$ and $C_y$, the response to large saccades have shown to be almost instant. In absence of a more precise model, each consecutive step can be based on a range of existing models, such as bisection.

In a further, refined, embodiment the above method includes a storage facility of coordinates to maintain history of real and reflected target positions, as well as a model of the real target position and its reflected position. The model allows dealing with the nonlinear relationship between real and reflected coordinates and provides a more accurate prediction of the best next position of IR-marker that to be used in the feedback loop.

Figure 17:
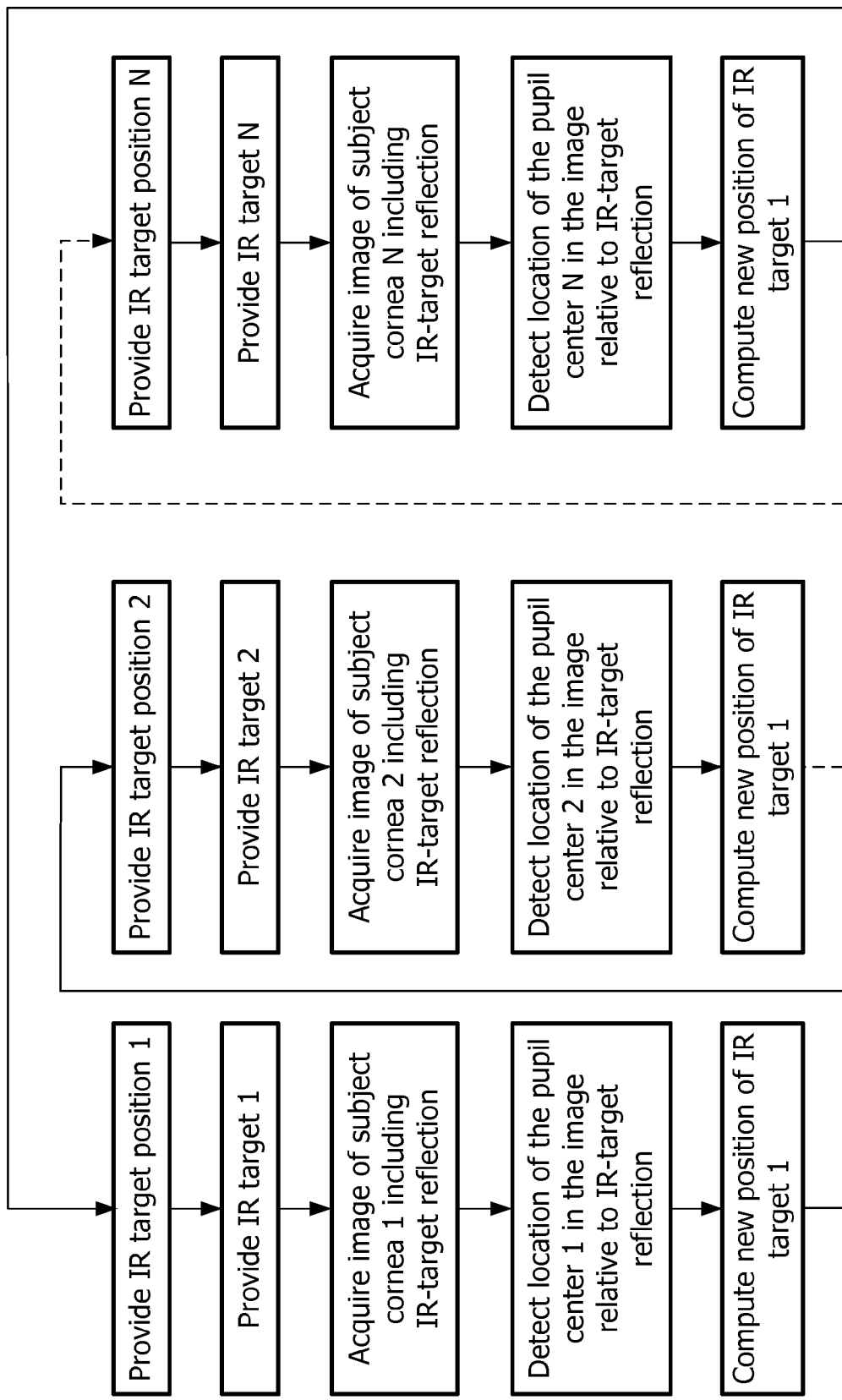
FIG. 17 illustrates a multi-observer method and system.

The invention can be embodied in many different ways. In the above embodiments use is made of one marker. In embodiments the detection of multiple eye-pairs indicates that multiple observers are detected; a situation typical to public displays and shop windows. Upon detection of each additional observer, the system adds an additional marker and updates the synchronisation with the camera such that detection and tracking is distributed in time over more observers. This system is illustrated in FIG. 17. The system of FIG. 17 allows to track the eye-gaze of multiple (N) observers by performing the IR-target presentation, image capture and gaze estimation in a time-sequential fashion. Note that the arrows indicate the order in time and not the flow of information. It is remarked that although different markers are used, there is a fundamental difference with the known system. The markers are movable and each marker has its own feedback and associated viewer. The advantage of this system is that the latency only increases when the number of simultaneously tracked observers increases.

The method and system in accordance with the invention can be used for a wide number of applications amongst which:

Calibration-free gaze tracking opens up a broad variety of applications; far beyond the traditional fields in which current gaze-tracking systems are applied. The absence of calibration means freedom of head movement with respect to the tracking device. Absence of calibration also means 'instantly-on' operation of the gaze tracking process.

In the field consumer products, calibration-free gaze tracking can have a variety of applications:

Control (Typically A Mouse Cursor In Combination With A Tangible Confirmation Button):

Provided that the gaze-tracker provides sufficient accuracy, various studies have shown that gaze-controlled is more efficient for point-and-click tasks than a conventional computer mouse. The increased reaction speed and accuracy of the method and system of the invention offers great advantage in this field.

For fixed devices, such as a (Internet-enabled) TV, the method and system of the invention offer robust cursor control for basic point-and-click actions, such that one-button web-surfing becomes possible 'from the couch'.

For handheld devices, the solution could free up the other hand, for those operations that currently require the usage of a stylus or the interaction with a touch-screen. Many handheld devices already comprise a camera so the invention can be relatively easily implemented in hand-held devices.

Devices can be made 'attentive', such that they respond to our actions (a button-press or a spoken command) only when you look at the device.

Communication:

There are various methods to transfer eye contact in video conferencing between two or more parties, many of which require the point of gaze of the individuals participating in the conference. In the past, existing gaze-tracking has been proven to be highly in-effective; a concept that has never left the laboratory due to the mentioned limitations of current systems. The increased speed and accuracy of the system and method of the invention when used for many parties greatly increases the efficiency.

We have confirmed user insights with regard to the relevance of eye contact during video calls.

In the field of health-care and wellness gaze-tracking provides a robust way to monitor the level of attention in hazardous tasks.

Control

Eye gaze still provides an important user interface to people that suffer from severe lack of motor skills; improving the quality of life by increasing their level of independence and wellbeing.

Eye gaze can provide contactless control in the operation room of a hospital, reducing a risk of contamination by tactile user interfaces.

Monitoring

The invention provides an unobtrusive way to monitor the level of attention during monotonic hazardous tasks such as driving a vehicle. An example is to monitor the visual attention of truck driver, using the windscreen as a medium to overlay a moving but imperceptible IR-target.

Simulators, such as driving or flying simulators. In simulators it is a great advantage if the gaze of the trainee can be monitored fast and accurate. In some simulators speed is of the highest importance, for instance in flight simulators or F1 racing simulators; a reliable and fast way of tracking the gaze of the F1 driver or fighter pilot is of the highest importance since important decisions are to be made in split-seconds by such persons.

Sports: much can be learned from the tracking the gaze of a person in such high speed sports as tennis, squash or contact sports. Improved training methods are made possible.

In the field of retail and digital signage, gaze tracking can be used to provide valuable feedback with regard to the observer's focus of attention.

Current-gaze tracking systems have already found their way to advertising agencies for the analysis of individual response to of printed and online adverts. The increased speed and accuracy of the system and method of invention will greatly expand the field of operation.

Gaze tracking is also being applied, to measure the collective real-life focal attention to a specific commercial display or poster by counting the pairs of gazing eyeballs as well as the duration of their attention.

The invention is not restricted to the display types shown.

An example of another display type that can advantageously be used in the method and system of the invention is an OLED display.

Figure 19:
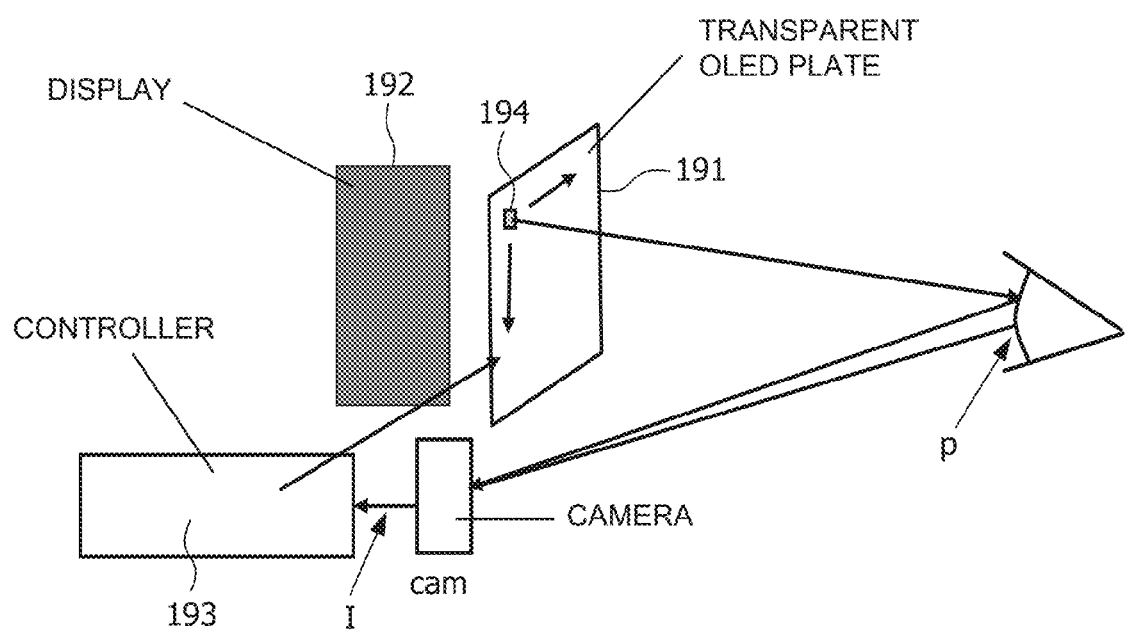
FIG. 19 illustrates schematically the use of a transparent OLED plate 191 in front of a display 192.

Using OLED technology, one can make a plate of transparent material emit light. OLED technology allows the material to emit IR light too. The OLED-material remains transparent for visible light but emits IR light. Using electrodes a matrix of IR OLED pixels can be made in a transparent layer. The IR OLED matrix acts much the same as a conventional OLED display, with this exception that it is transparent to visible light and emits addressable pixels in IR. The IR marker is addressed by an active grid of OLED IR pixels and the position is variable dependent on the addressing of the IR pixels. FIG. 19 illustrates schematically the use of a transparent OLED plate 191 in front of a display 192.

The OLED matrix is addressed using a controller 193. The controller 193 receives information I. This information I is dependent on the measurements taken from the image taken by camera CAM. The matrix of OLED pixels provide for an IR marker 194 on the transparent OLED material.

The advantage of a transparent view-through screen, as for any screen that can be put in front of a display or scene, is that it can be used for any existing display or scene.

This transparent layer can be used as a screen in front of a display, or in front of a scene. Using an OLED transparent screen has the advantage that the addressing speed of an OLED is remarkably high allowing even faster gaze tracking.

The invention is not restricted to the given exemplary embodiments.

For instance when use is made of a projected marker, the marker can be projected on a display screen, on a transparent screen through which the observer watches a scene or a display device, or directly on the scene.

Figure 18:
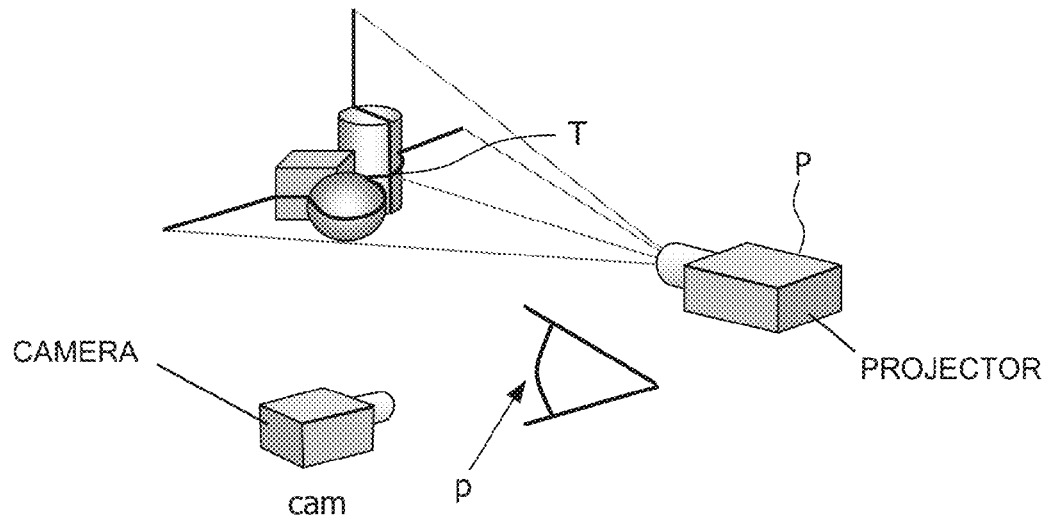
FIG. 18 illustrates an embodiment in which the projector projects an IR target on a scene.

FIG. 18 illustrates an embodiment in which the projector P projects an IR target on a scene, in this example represented by the centre of a cross on the scene. In FIG. 18 the target is centred on the cylinder. The camera is also shown. The camera takes an image of the eye and more in particular the corneal reflection of the IR target and the pupil's centre.

The invention can be used to track the gaze of more than one person as explained above. The invention can also be used to track the gaze direction of both eyes of the same person. In said embodiments an image is taken of the left and right eye and the corneal reflection on one or both of the eyes is measured and for at least one of the eyes a marker is produced. In embodiments for both eyes a marker can be used, in which case the gaze of both eyes can be independent monitored. Alternatively the gaze of one eye is tracked and for the other eye the deviation of gaze is measured or estimated. An application is for instance a device for measuring in a quantitative manner the 'laziness' of a lazy eye. A child is provided with a pair of glasses with two cameras, wherein one small camera takes images of the left eye and another one of the right eye. Alternatively the cameras can both be at some distance from the child. It is also possible to use a single camera to record both images. The child is asked to play a video game wherein it must follow a certain target with his eyes. This will happen automatically if he/she has to catch an object with the cursor or lead an animated figure through a maze. The movements of both eyes are measured. In a completely unobtrusive way for both eyes the reaction time of the eye to the movement of the animated figure can be measured providing a measure for the laziness of both eyes and the coordination of both eyes to the movements. In a fun way for the child the laziness of the eyes can be quantitatively measured. Progress of treatment of the lazy eye can be tracked without any discomfort to the child.

Another application is to monitor for both eyes the movements for a driver looking through a windshield, wherein on the windshield an IR target is provided. In a normal state of alertness both eyes will cooperate and make a certain pattern of movement to keep track of what is happening on the road in front of the driver. It is also possible to measure the convergence of the eyes. When the driver is tired this will show in the movements of the eyes and the coordination between the eyes and a signal can be given to the driver to take a rest.

When the gaze of both eyes is tracked it is possible to determine the gaze of each eye, the difference in gaze between the eyes, as well as the average gaze as the average of both eyes. In such a application the marker is not itself projected on the observed object, the road, or part of the observed image on a display screen but is still associated with the observed object in that the marker indicates the position of the observed object. The direction of gaze is in line with the position of the marker on the windshield.

The convergence angle of an eye pair can be used to estimate the distance from which an observer is looking at an object. This is especially useful in a monitoring scenario (e.g. monitoring the gaze of a truck driver, or a customer viewing a shop window).

The latency of the system is dependent on the number of eyes to be tracked. We can reduce the latency by employing a single marker for each observer (eye pair).

Averaging the two displacement vectors (one for each eye) yields the update vector. The marker position is then updated with this average. Since an observer's eyes will converge (assuming normal vision) towards the same location, any residual error is distributed symmetrically over the eye pair. The amplitude of displacement vectors versus update vector correlates to convergence. When looking directly at the marker, all vectors will be zero (when the system has converged). When looking at a more distant object than the marker (projection) plane, the horizontal displacement vector will be negative for one eye and equally positive for the other.

Another application involves the possibility to extend the principle beyond human or animal eyes, to include artificial eyes, for example in the case of robots. It is known that the principle of red eye effect applies to cameras, regardless of the particular lens mounted on them. On the other hand, the coincidence of the light source reflection with the centre of the camera pupil is due to the particular reflection index of the tissues present in human and animal eyes. It would be possible to design special optical configurations which would maintain such coincidence, while at the same time allow obtaining the desired optical properties. The application of such special lenses would be multiple. If adopted in the case of robots, it would allow detecting their point of gaze. A different application would exploit these lenses as markers, instead of lenses. In this context, the optical elements would be applied on the surface of any object, as markers, allowing establishing the orientation of the object surface, exploiting the same principle used in the described gaze tracking system.

In short the invention can be described by:

A system for tracking the point of gaze of an observer observing an object comprises a camera for recording an image of an eye of the observer, comprises a means for providing a luminous marker, and means for analyzing the image of the eye to determine the reflection of the marker on the eye and the centre of the pupil. The relative positions of the corneal reflection of the marker and the pupil centre are measured. The marker is repositioned, in dependence on the determined relative positions, to improve correspondence between the corneal reflection of the marker and the pupil centre.

The short description of the method corresponds to the above description of the system.

In the claims, any reference signs placed between parentheses shall not be construed as limiting the claim.

The word "comprising" does not exclude the presence of other elements or steps than those listed in a claim. The invention may be implemented by any combination of features of various different preferred embodiments as described above.

A camera is any device for recording images.

It could be a part of a device also used for other purposes such as communication, or attached to, integrated in or cooperating with such a communication device.

Means for analyzing, means for addressing, means for calculating etc. can be in the form of hard-ware, soft-ware or any combination thereof.

Where use is made of the method and system any such means can be present in or near the camera or in a device at or near the scene to which the camera is connected. However, image data can also be analysed remotely, as can the markers be controlled remotely. For instance, in a store, several cameras can observe several spots, each spot being for instance a window display, wherein at each spot several observers can be tracked. The calculation of the difference between markers and pupil centres and the calculation of the move to be made by each marker and the signal to be send to move the markers, can be processed on a central computer within the store, or even, in case the same is done in various stores throughout the country, at a central computer at head quarters or at a central server.

The invention also relates to computer programs comprising program code means for performing a method according to the invention when said program is run on a computer, as well as computer program product comprising program code means stored on a computer readable medium for performing a method according to the invention.

The invention claimed is:

1. A system for tracking a point of gaze of an observer observing an object, wherein the system comprises:
    a device for recording an image of an eye of the observer;
    a light source configured to provide a luminous marker on or associated with the observed object, said marker being selectively movable within a field of view of the observer; and
    a control unit comprising a first image analyzer configured to analyze the image recorded by the image recording device, said first image analyzer being configured to determine, from the image, a corneal reflection of the marker on the eye of the observer and a center of a pupil of the eye of the observer,
    wherein the system for tracking further comprises:
    said first image analyzer being configured to determine relative positions of the corneal reflection of the marker and the pupil center;
    said control unit comprising a second analyzer configured to receive the determined relative positions of the corneal reflection of the marker and the pupil center, and configured to generate data for repositioning the marker in order to lessen a difference between the determined relative positions of the corneal reflection of the marker and the pupil, until the position of the corneal reflection of the marker and the position of the pupil substantially coincide; and
    means for repositioning the marker in response to the repositioning data.

2. The system as claimed in claim 1, wherein the system further comprises a display device, and the position of the marker is related to the display device.

3. The system as claimed in claim 2, wherein the display device and the light source for providing the marker are integrated into a single device.

4. The system as claimed in claim 2, wherein the display device and the light source for providing the marker are separate devices.

5. The system as claimed in claim 4, wherein the light source for providing the marker comprises a transparent shield positioned in front of an image screen of the display device.

6. The system as claimed in claim 1, wherein the light source for providing the marker provides an infrared (IR) marker.

7. The system as claimed in claim 1, wherein the marker is shaped in a pattern.

8. The system as claimed in claim 1, wherein the light source for providing the marker and the repositioning means for repositioning the marker provide and reposition the marker in or on a transparent plate in front of a scene including the object.

9. The system as claimed in claim 8, wherein the transparent plate is a windshield of a vehicle.

10. The system as claimed in claim 8, wherein the transparent plate is a shop window.

11. The system as claimed in claim 3, wherein the light source for providing the marker provides the marker in an image displayed on a display screen of the display device.

12. The system as claimed in claim 11, wherein the marker is an IR marker.

13. The system as claimed in claim 11, wherein the system comprises a Liquid Crystal Display device having an infrared (IR) backlight and a visible light backlight.

14. The system as claimed in claim 1, wherein the light source for providing the marker comprise a transparent OLED screen for providing a marker.

15. The system as claimed in claim 1, wherein the system is arranged to track the gaze of more than one observer, said system providing a respective additional single marker for each additional observer.

16. A method for tracking the point of gaze of an observer observing an object, wherein the method comprises:
    recording an image of an eye of the observer;
    providing a luminous marker on or associated with the observed object, said marker being selectively movable within a field of view of the observer; and
    analyzing the image recorded by the image recording device in order to determine, from the image, a corneal reflection of the marker and a center of a pupil of the eye of the observer, wherein the method further comprises:
    determining relative positions of the corneal reflection of a marker and the pupil center;
    generating data for repositioning the marker in order to lessen a difference between the determined relative positions of the corneal reflection of the marker and the pupil; and
    repositioning the marker in response to the repositioning data.

17. The method as claimed in claim 16, wherein the marker is shaped in a pattern.

18. The method as claimed in claim 16, wherein the marker is provided in or on a transparent plate.

* * * * *